United States Patent
Pal et al.

(10) Patent No.: US 11,168,301 B2
(45) Date of Patent: Nov. 9, 2021

(54) METHOD FOR PRODUCING PHOTORECEPTOR CELLS, RETINAL PIGMENTED EPITHELIAL CELLS, AND RETINAL ORGANOIDS

(71) Applicant: Eyestem Research Private Limited, Gujarat (IN)

(72) Inventors: Rajarshi Pal, Bangalore (IN); Rajani Battu, Bangalore (IN); Reena Rathod, Bangalore (IN); Harshini Surendran, Tamil Nadu (IN); Kapil Bharti, Potomac, MD (US); Deepak Lamba, San Anselmo, CA (US); Dhruv Sareen, Northridge, CA (US); Mahendra Rao, Timonium, MD (US); Sushma Nanjunda Swamy, Bangalore-Karnataka (IN); Vijay Bhaskar Konala Reddy, Vishakapatnam-Andhra Pradesh (IN); Mohanapriya Rajamoorthy, Tamil Nadu (IN)

(73) Assignee: EYESTEM RESEARCH PRIVATE LIMITED, Ahmedabad (IN)

( * ) Notice: Subject to any disclaimer, the term of this patent is extended or adjusted under 35 U.S.C. 154(b) by 0 days.

(21) Appl. No.: 16/340,185

(22) PCT Filed: Oct. 5, 2018

(86) PCT No.: PCT/IN2018/050634
§ 371 (c)(1),
(2) Date: Apr. 8, 2019

(87) PCT Pub. No.: WO2019/069327
PCT Pub. Date: Apr. 11, 2019

(65) Prior Publication Data
US 2020/0224159 A1  Jul. 16, 2020

(30) Foreign Application Priority Data
Oct. 5, 2017  (IN) .............. 201721035392

(51) Int. Cl.
| C12N 5/00 | (2006.01) |
|---|---|
| C12N 5/079 | (2010.01) |
| A61K 35/30 | (2015.01) |
| A61K 35/545 | (2015.01) |
| C12N 5/073 | (2010.01) |
| C12N 5/0735 | (2010.01) |
| C12N 5/0793 | (2010.01) |
| C12N 5/0797 | (2010.01) |

(52) U.S. Cl.
CPC ............ *C12N 5/0621* (2013.01); *A61K 35/30* (2013.01); *A61K 35/545* (2013.01); *C12N 5/062* (2013.01); *C12N 5/0603* (2013.01); *C12N 5/0606* (2013.01); *C12N 5/0623* (2013.01); *C12N 2501/395* (2013.01); *C12N 2501/415* (2013.01); *C12N 2501/42* (2013.01); *C12N 2501/727* (2013.01); *C12N 2501/734* (2013.01); *C12N 2506/45* (2013.01); *C12N 2513/00* (2013.01); *C12N 2533/52* (2013.01)

(58) Field of Classification Search
CPC .. C12N 5/0621; C12N 5/0603; C12N 5/0606; C12N 5/062
USPC ......................................................... 435/325
See application file for complete search history.

(56) References Cited

U.S. PATENT DOCUMENTS

| 7,993,920 B2 | 8/2011 | Martinson et al. |
|---|---|---|
| 8,956,866 B2 | 2/2015 | Idelson et al. |
| 9,850,463 B2 * | 12/2017 | Hikita ................. C12N 5/0621 |
| 10,287,546 B2 | 5/2019 | Chambers et al. |
| 2017/0175077 A1 | 6/2017 | Nishino et al. |

FOREIGN PATENT DOCUMENTS

| WO | 2015/054526 A2 | 4/2015 |
|---|---|---|
| WO | 2017091844 A1 | 6/2017 |

OTHER PUBLICATIONS

Osakada (J. Cell Sci., 2009, vol. 122, p. 3169-3179).*
Int'l Search Report and Written Opinion dated Dec. 5, 2018 in Int'l Application No. PCT/IN2018/050634.
Fumitaka et al., "In vitro differentiation of retinal cells from human pluripotent stem cells by small-molecule induction," Journal of Cell Science, vol. 122, No. 17, pp. 3169-3179 (Sep. 1, 2009).
Song et al., "Looking into the future: Using induced pluripotent stem cells to build two and three dimensional ocular tissue for cell therapy and disease modeling," Brain Research, vol. 1638, pp. 2-14 (Dec. 17, 2015).
Chen et al., "Three-dimensional retinal organoids from mouse pluripotent stem cells mimic in vivo development with enhanced stratification and rod photoreceptor differentiation," Molecular Vision, vol. 22, pp. 1077-1094 (Sep. 9, 2016).
Gonzalez-Cordero et al., "Photoreceptor precursors derived from three-dimensional embryonic stem cell cultures integrate and mature within adult degenerate retina," Nature Biotechnology, vol. 31, No. 8, pp. 741-747 (Jul. 21, 2013).
Miyagishima et al., "In Pursuit of Authenticity: Induced 21-23 Pluripotent Stem Cell-Derived Retinal Pigment Epithelium for Clinical Applications: Authentication of iPSC-Derived RPE," Stem Cells Translational Medicine, vol. 5, No. 11 (Jul. 11, 2016).
May-Simera et al., "Primary Cilium-Mediated Retinal Pigment Epithelium Maturation Is Disrupted in Ciliopathy Patient Cells," Cell Reports, vol. 22, No. 1, pp. 189-205 (Jan. 2, 2018).

(Continued)

*Primary Examiner* — Michael C Wilson
(74) *Attorney, Agent, or Firm* — Panitch Schwarze Belisario & Nadel LLP

(57) ABSTRACT

A unified cell differentiation protocol for obtaining photoreceptor cells, retinal pigment epithelium, and 3D retinal organoid from pluripotent stem cells is described. Also described are photoreceptor cells, retinal pigmented epithelium, and 3D retinal organoid obtained from pluripotent stem cells. Also described are a pharmaceutical composition and a medicament containing the photoreceptor cells, retinal pigment epithelium, and 3D retinal organoid as described.

5 Claims, 7 Drawing Sheets
Specification includes a Sequence Listing.

(56) References Cited

OTHER PUBLICATIONS

Surendran et al., Transplantation of retinal pigment epithelium and photoreceptors generated concomitantly via small molecule-mediated differentiations rescues visual function in rodent models of retinal degeneration, 12(70) Stem Cell Research & Therapy (2021).
Volkner et al., Retinal Organoids from Pluripotent Stem Cells Efficiently Recapitulate Retinogenesis, 6 Stem Cell Reports 525-538 (Apr. 12, 2016).
Regent et al., A simple and efficient method for generating human retinal organoids, 29 Molecular Vision 97-105 (2020).
Schwartz et al., Embryonic stem cell trials for macular degeneration: a preliminary report, 379 The Lancet 713-720 (Feb. 25, 2012).
Shrestha et al., Aberrant hiPSCs-Derived from Human Keratinocytes Differentiates into 3D Retinal Organoids that Acquire Mature Photoreceptors, 8(36) Cells 1-22 (2019).
Simo et al.. The Retinal Pigment Epithelium: Something More than a Constituent of the Blood-Retinal Barrier-Implications for the Pathogenesis of Diabetic Retinopathy, 2010 Journal of Biomedicine and Biotechnology 1-15 (Feb. 2010).
Veleri et al., Biology and therapy of inherited retinal degenerative disease: insights from mouse models, 8 Disease Models & Mechanisms 109-129 (2015).

* cited by examiner

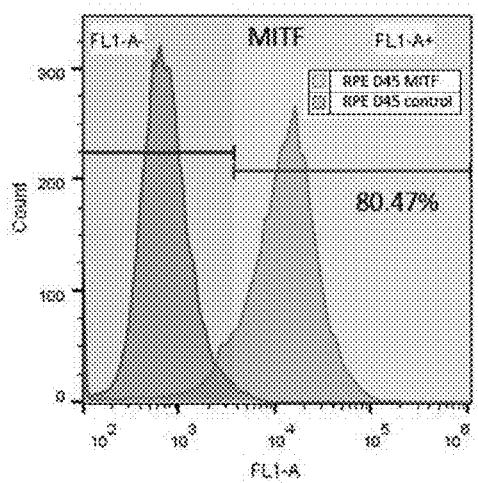 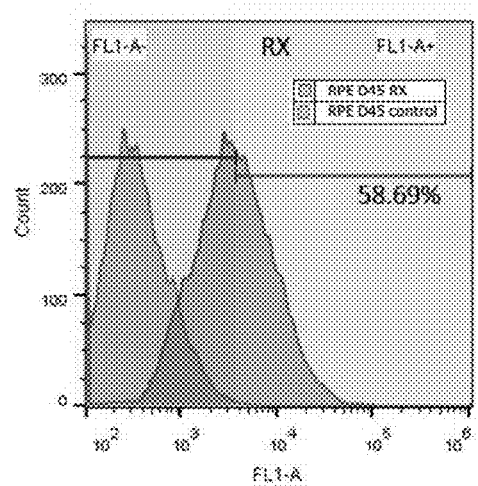
Figure 6A  Figure 6B
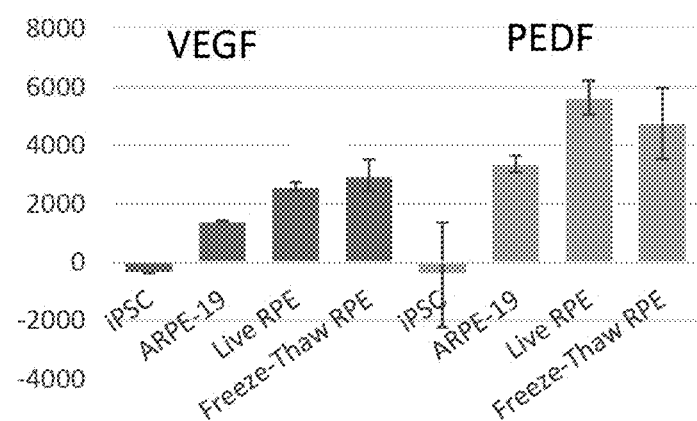
Figure 6C

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Primer sequence of hPAX6 F

<400> SEQUENCE: 1
agttcttcgc aacctggcta                                              20

<210> SEQ ID NO 2
<211> LENGTH: 20
<212> TYPE: DNA
<213> ORGANISM: Artificial Sequence
<220> FEATURE:
<223> OTHER INFORMATION: Primer sequence of hPAX6 R

<400> SEQUENCE: 2
tggtattctc tccccctcct                                              20

<210> SEQ ID NO 3
<211> LENGTH: 20
<212> TYPE: DNA
<213> ORGANISM: Artificial Sequence
<220> FEATURE:
<223> OTHER INFORMATION: Primer Sequence of hZO-1 F

<400> SEQUENCE: 3
tgaggcagct cacataatgc                                              20

<210> SEQ ID NO 4
<211> LENGTH: 20
<212> TYPE: DNA
<213> ORGANISM: Artificial Sequence
<220> FEATURE:
<223> OTHER INFORMATION: Primer Sequence hZO-1R

<400> SEQUENCE: 4
gggagttggg gttcataggt                                              20
```

-continued

```
<210> SEQ ID NO 5
<211> LENGTH: 20
<212> TYPE: DNA
<213> ORGANISM: Artificial Sequence
<220> FEATURE:
<223> OTHER INFORMATION: Primeer Sequence hSIX3 F

<400> SEQUENCE: 5
ccggaagagt tgtccatgtt                                               20

<210> SEQ ID NO 6
<211> LENGTH: 20
<212> TYPE: DNA
<213> ORGANISM: Artificial Sequence
<220> FEATURE:
<223> OTHER INFORMATION: Primer Sequence hSIX3 R

<400> SEQUENCE: 6
cgactcgtgt ttgttgatgg                                               20

<210> SEQ ID NO 7
<211> LENGTH: 20
<212> TYPE: DNA
<213> ORGANISM: Artificial Sequence
<220> FEATURE:
<223> OTHER INFORMATION: Primer Sequence hLHX2 F

<400> SEQUENCE: 7
gctcgggact tggtttatca                                               20

<210> SEQ ID NO 8
<211> LENGTH: 20
<212> TYPE: DNA
<213> ORGANISM: Artificial Sequence
<220> FEATURE:
<223> OTHER INFORMATION: Primer Sequence hLHX2 R

<400> SEQUENCE: 8
gttgaagtgt gcggggtact                                               20

<210> SEQ ID NO 9
<211> LENGTH: 20
<212> TYPE: DNA
<213> ORGANISM: Artificial Sequence
<220> FEATURE:
<223> OTHER INFORMATION: Primer sequence hRX F

<400> SEQUENCE: 9
gaacagccca agaaaaagca                                               20

<210> SEQ ID NO 10
<211> LENGTH: 20
<212> TYPE: DNA
<213> ORGANISM: Artificial Sequence
<220> FEATURE:
<223> OTHER INFORMATION: Primer Sequence hRX R

<400> SEQUENCE: 10
gctgtacacg tccgggtagt                                               20

<210> SEQ ID NO 11
<211> LENGTH: 20
<212> TYPE: DNA
<213> ORGANISM: Artificial Sequence
<220> FEATURE:
<223> OTHER INFORMATION: Primer Sequence hMITF F
```

<400> SEQUENCE: 11
ccaggcatga acacacattc                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer Sequence hMITF R

<400> SEQUENCE: 12
tccatcaagc ccaagatttc                                                 20

<210> SEQ ID NO 13
<211> LENGTH: 20
<212> TYPE: DNA
<213> ORGANISM: Artificial Sequence
<220> FEATURE:
<223> OTHER INFORMATION: Primr Sequence hRPE65 F

<400> SEQUENCE: 13
gatctctgct gctggaaagg                                                 20

<210> SEQ ID NO 14
<211> LENGTH: 20
<212> TYPE: DNA
<213> ORGANISM: Artificial Sequence
<220> FEATURE:
<223> OTHER INFORMATION: Primer Sequence hRPE65 R

<400> SEQUENCE: 14
tggggagcgt gactaaattc                                                 20

<210> SEQ ID NO 15
<211> LENGTH: 20
<212> TYPE: DNA
<213> ORGANISM: Artificial Sequence
<220> FEATURE:
<223> OTHER INFORMATION: Primer Sequence hBESTROPHIN F

<400> SEQUENCE: 15
ggcagaacac aagcagttgg                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer Sequence hBESTROPHIN R

<400> SEQUENCE: 16
acgcaaggtg ttcatctcgt                                                 20

<210> SEQ ID NO 17
<211> LENGTH: 20
<212> TYPE: DNA
<213> ORGANISM: Artificial Sequence
<220> FEATURE:
<223> OTHER INFORMATION: Primer Sequence hTYROSINASE F

<400> SEQUENCE: 17
acccattgga cataaccggg                                                 20

<210> SEQ ID NO 18
<211> LENGTH: 22

```
<212> TYPE: DNA
<213> ORGANISM: Artificial Sequence
<220> FEATURE:
<223> OTHER INFORMATION: Primer Sequence hTYROSINASE R

<400> SEQUENCE: 18
agagtctggg tctgaatctt gt                                              22

<210> SEQ ID NO 19
<211> LENGTH: 21
<212> TYPE: DNA
<213> ORGANISM: Artificial Sequence
<220> FEATURE:
<223> OTHER INFORMATION: Primer Sequence hEZRIN F

<400> SEQUENCE: 19
tcaatgtccg agttaccacc a                                               21

<210> SEQ ID NO 20
<211> LENGTH: 20
<212> TYPE: DNA
<213> ORGANISM: Artificial Sequence
<220> FEATURE:
<223> OTHER INFORMATION: Primer Sequence hEZRIN R

<400> SEQUENCE: 20
ggccaaagta ccacacttcc                                                 20

<210> SEQ ID NO 21
<211> LENGTH: 20
<212> TYPE: DNA
<213> ORGANISM: Artificial Sequence
<220> FEATURE:
<223> OTHER INFORMATION: Primer Sequence hDCT F

<400> SEQUENCE: 21
ggttcctttc ttccctccag                                                 20

<210> SEQ ID NO 22
<211> LENGTH: 20
<212> TYPE: DNA
<213> ORGANISM: Artificial Sequence
<220> FEATURE:
<223> OTHER INFORMATION: Primer Sequence hDCT R

<400> SEQUENCE: 22
aaccaaagcc accagtgttc                                                 20

<210> SEQ ID NO 23
<211> LENGTH: 19
<212> TYPE: DNA
<213> ORGANISM: Artificial Sequence
<220> FEATURE:
<223> OTHER INFORMATION: Primer Sequence hNrl F

<400> SEQUENCE: 23
atgtggattg gacgacttc                                                  19

<210> SEQ ID NO 24
<211> LENGTH: 18
<212> TYPE: DNA
<213> ORGANISM: Artificial Sequence
<220> FEATURE:
<223> OTHER INFORMATION: Primer Sequence hNrl R

<400> SEQUENCE: 24
```
ttggcgagat tgtcttgg					18

<210> SEQ ID NO 25
<211> LENGTH: 19
<212> TYPE: DNA
<213> ORGANISM: Artificial Sequence
<220> FEATURE:
<223> OTHER INFORMATION: Primer Sequence hTRB2 F

<400> SEQUENCE: 25
acaggagatt tcattcggg					19

<210> SEQ ID NO 26
<211> LENGTH: 22
<212> TYPE: DNA
<213> ORGANISM: Artificial Sequence
<220> FEATURE:
<223> OTHER INFORMATION: Primer Sequence hTRB2 R

<400> SEQUENCE: 26
ttgtaagact atcatctggg tg				22

<210> SEQ ID NO 27
<211> LENGTH: 20
<212> TYPE: DNA
<213> ORGANISM: Artificial Sequence
<220> FEATURE:
<223> OTHER INFORMATION: Primr Sequence hBLIMP1 F

<400> SEQUENCE: 27
gtggtattgt cgggactttg					20

<210> SEQ ID NO 28
<211> LENGTH: 20
<212> TYPE: DNA
<213> ORGANISM: Artificial Sequence
<220> FEATURE:
<223> OTHER INFORMATION: Primer Seqeunce hBLIMP1 R

<400> SEQUENCE: 28
ggttgcttta gactgctctg					20

<210> SEQ ID NO 29
<211> LENGTH: 21
<212> TYPE: DNA
<213> ORGANISM: Artificial Sequence
<220> FEATURE:
<223> OTHER INFORMATION: Primer Seqeunce hCHX10 F

<400> SEQUENCE: 29
cgacacagga caatctttac c					21

<210> SEQ ID NO 30
<211> LENGTH: 20
<212> TYPE: DNA
<213> ORGANISM: Artificial Sequence
<220> FEATURE:
<223> OTHER INFORMATION: Primer Sequence hCHX10 R

<400> SEQUENCE: 30
catagacgtc tgggtagtgg					20

<210> SEQ ID NO 31
<211> LENGTH: 20
<212> TYPE: DNA
<213> ORGANISM: Artificial Sequence

```
<220> FEATURE:
<223> OTHER INFORMATION: Primer Sequence hBRN3 F

<400> SEQUENCE: 31
ctcgctcgaa gcctactttg                                              20

<210> SEQ ID NO 32
<211> LENGTH: 19
<212> TYPE: DNA
<213> ORGANISM: Artificial Sequence
<220> FEATURE:
<223> OTHER INFORMATION: Primer Sequence hBRN3 R

<400> SEQUENCE: 32
gacgcgcacc acgtttttc                                               19

<210> SEQ ID NO 33
<211> LENGTH: 21
<212> TYPE: DNA
<213> ORGANISM: Artificial Sequence
<220> FEATURE:
<223> OTHER INFORMATION: Primr Sequence hSOX-2 F

<400> SEQUENCE: 33
ccgcgtcaag cggcccatga a                                            21

<210> SEQ ID NO 34
<211> LENGTH: 22
<212> TYPE: DNA
<213> ORGANISM: Artificial Sequence
<220> FEATURE:
<223> OTHER INFORMATION: Primer Sequence hSOX-2 R

<400> SEQUENCE: 34
gccgcttctc cgtctccgac aa                                           22

<210> SEQ ID NO 35
<211> LENGTH: 25
<212> TYPE: DNA
<213> ORGANISM: Artificial Sequence
<220> FEATURE:
<223> OTHER INFORMATION: Primer sequence h beta actin F

<400> SEQUENCE: 35
tcacccacac tgtgcccatc tacga                                        25

<210> SEQ ID NO 36
<211> LENGTH: 25
<212> TYPE: DNA
<213> ORGANISM: Artificial Sequence
<220> FEATURE:
<223> OTHER INFORMATION: Primr Sequence h beta actin R

<400> SEQUENCE: 36
cagcggaacc gctcattgcc aatgg                                        25
```

METHOD FOR PRODUCING PHOTORECEPTOR CELLS, RETINAL PIGMENTED EPITHELIAL CELLS, AND RETINAL ORGANOIDS

CROSS-REFERENCE TO RELATED APPLICATION

This application is a Section 371 of International Application No. PCT/IN2018/050634, filed Oct. 5, 2018, not yet published and claims priority under 35 U.S.C. § 119(b) to India Application No. 201721035392, filed Oct. 5, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 689370_2US", creation date of Apr. 2, 2019, and having a size of 7.1 KB. The sequence listing submitted via EFS-Web is part of the specification and is herein incorporated by reference in its entirety.

FIELD OF INVENTION

The present disclosure relates to the field of cell culture techniques and cell differentiation protocols in general and cell differentiation protocol for producing multiple retinal cells in particular.

BACKGROUND OF THE INVENTION

Retina is a layered structure and forms the third and inner coat of the eye. It is a light sensitive layer of tissue and comprises multiple cells with varying functions. Photoreceptor cells are the only neurons in the retina that are directly sensitive to light and function by converting light to signals that can stimulate biological processes. Rods, cones and photosensitive retinal ganglion cells are the three different types of photoreceptor cells found in the human eye.

RPE or retinal pigmented epithelium comprises cells which interact closely with the photoreceptors for the purpose of visual function. RPE is also responsible for transport of nutrients, ions and water, phagocytosis of shed photoreceptor membranes and for secretion of essential factors for the structural integrity of the retina (Simo et al. Journal of Biomedicine and Biotechnology, 2010, 15 Article ID 190724).

Due to their association with major complex functions, the photoreceptor cells and the RPE cells are the most important cells of the retina and malfunctioning of any of the two cells leads to development of serious eye defects. Genetic components determine the genesis and health of photoreceptors, and mutations that lead to structural and/or functional perturbations can eventually lead to blindness (Veleri et al. Dis Model Mech. 2015. 8(2: 109-129).

Retinal degeneration is described as the destruction or deterioration of the retina caused by progressive and eventual death of the retinal cells. The disorders associated with retinal degeneration are collectively termed as retinal degenerative disorders. Diabetic retinopathy, retinopathy of prematurity, macular degeneration, Usher syndrome, Stargardt disease and Retinis Pigmentosa are few of the prevalent retinal degenerative diseases.

WO2017091844 A1 provides a differentiation protocol to generate retinal pigmented epithelial cells for the in vitro differentiation of mammalian pluripotent stem cells to mature, functional retinal pigment epithelial cells.

U.S. Pat. No. 8,956,866 B2 describes a method of promoting directed differentiation of human pluripotent stem cells into retinal pigment epithelium fate.

Recent years have witnessed multiple cases of retinal degenerative disorders. Constant efforts are being made in this field and a number of protocols have also been designed for production of retinal cells. However, most of these methods are time consuming and tend to be inefficient. Therefore, there is a need for developing protocols for generating retinal cells that are not only efficient but are also cost effective.

SUMMARY OF INVENTION

In an aspect of the present disclosure, there is provided a method for producing multiple cell types of retina from pluripotent stem cells, said method comprising: (a) generating non-adherent suspension embryoid bodies from the pluripotent stem cells in a medium A, wherein the medium A comprises growth factors, organic molecules, and lipid concentrates; (b) culturing the non-adherent suspension embryoid bodies in a medium B for 3-5 days, wherein the medium B comprises at least one WNT pathway inhibitor and at least one ALK receptor inhibitor; (c) culturing the embryoid bodies of step (b) on plates coated with at least one suitable extracellular matrix in the medium B for 4-8 days; (d) culturing the embryoid bodies or adherent cultures of step (c) in a medium C for 5-20 days to form neural rosette like structures and epithelial like retinal progenitor cells, wherein the medium C does not comprise any inhibitor; (e) selecting the neural rosette like structures using a selection reagent, wherein the selection reagent allows preferential isolation and enrichment of the neural rosette like structures; (f) culturing the neural rosette like structures of step (e) on plates coated with at least one suitable extracellular matrix in a modified medium C until confluence for formation of photoreceptor progenitors, wherein the modified medium C comprises at least one ROCK1 inhibitor and NOTCH inhibitor; (g) culturing the photoreceptor progenitors in the modified medium C for 8-12 weeks to form mature photoreceptor cells; (h) selecting and culturing the epithelial like retinal progenitor cells obtained in step (d) in the medium C for 5-7 days for formation of retinal pigmented epithelial progenitors; (i) culturing the retinal pigmented epithelial progenitors of step (h) in a medium D for 15-45 days to obtain mature retinal pigmented epithelial cells, wherein the medium D comprises taurine, hydrocortisone and triido-thyronine; (j) culturing the non-adherent suspension embryoid bodies of step (a) in the medium B for 8-10 days; and (k) culturing the non-adherent suspension embryoid bodies of step (j) in the medium C for 8-12 weeks for formation of 3D retinal organoids, wherein the method is a unified method for producing multiple cell types of retina.

In an aspect of the present disclosure, there is provided a method for producing multiple cell types of retina from pluripotent stem cells, said method comprising: (a) obtaining adherent cultures by direct differentiation from the pluripotent stem cells in a medium A, wherein the medium A comprises growth factors, organic molecules, and lipid concentrates; (b) culturing the adherent cultures in a medium B for 3-5 days, wherein the medium B comprises at least one WNT pathway inhibitor and at least one ALK receptor inhibitor; (c) culturing the adherent cultures of step (b) on plates coated with at least one suitable extracellular matrix in the medium B for 4-8 days; (d) culturing the embryoid bodies or adherent cultures of step (c) in a medium C for 5-20 days to form neural rosette like structures and epithelial like retinal progenitor cells, wherein the medium C does not comprise any inhibitor; (e) selecting the neural rosette like structures using a selection reagent, wherein the selection reagent allows preferential isolation and enrichment of the neural rosette like structures; (f) culturing the neural rosette like structures of step (e) on plates coated with at least one suitable extracellular matrix in a modified medium C until confluence for formation of photoreceptor progenitors, wherein the modified medium C comprises at least one ROCK1 inhibitor and NOTCH inhibitor; (g) culturing the photoreceptor progenitors in the modified medium C for 8-12 weeks to form mature photoreceptor cells; (h) selecting and culturing the epithelial like retinal progenitor cells obtained in step (d) in the medium C for 5-7 days for formation of retinal pigmented epithelial progenitors; (i) culturing the retinal pigmented epithelial progenitors of step (h) in a medium D for 15-45 days to obtain mature retinal pigmented epithelial cells, wherein the medium D comprises taurine, hydrocortisone and triiodo-thyronine, and wherein the method is a unified method for producing multiple cell types of retina.

In an aspect of the present disclosure, there is provided a pharmaceutical composition comprising photoreceptor cells obtained from any one method as described herein above.

In an aspect of the present disclosure, there is provided a pharmaceutical composition comprising retinal pigmented epithelial cells obtained from any one method as described herein above.

In an aspect of the present disclosure, there is provided a pharmaceutical composition comprising 3D retinal organoids obtained from a method comprising: (a) generating non-adherent suspension embryoid bodies from the pluripotent stem cells in a medium A, wherein the medium A comprises growth factors, organic molecules, and lipid concentrates; (b) culturing the non-adherent suspension embryoid bodies in a medium B for 3-5 days, wherein the medium B comprises at least one WNT pathway inhibitor and at least one ALK receptor inhibitor; (c) culturing the embryoid bodies of step (b) on plates coated with at least one suitable extracellular matrix in the medium B for 4-8 days; (d) culturing the embryoid bodies or adherent cultures of step (c) in a medium C for 5-20 days to form neural rosette like structures and epithelial like retinal progenitor cells, wherein the medium C does not comprise any inhibitor; (e) selecting the neural rosette like structures using a selection reagent, wherein the selection reagent allows preferential isolation and enrichment of the neural rosette like structures; (f) culturing the neural rosette like structures of step (e) on plates coated with at least one suitable extracellular matrix in a modified medium C until confluence for formation of photoreceptor progenitors, wherein the modified medium C comprises at least one ROCK1 inhibitor and NOTCH inhibitor; (g) culturing the photoreceptor progenitors in the modified medium C for 8-12 weeks to form mature photoreceptor cells; (h) selecting and culturing the epithelial like retinal progenitor cells obtained in step (d) in the medium C for 5-7 days for formation of retinal pigmented epithelial progenitors; (i) culturing the retinal pigmented epithelial progenitors of step (h) in a medium D for 15-45 days to obtain mature retinal pigmented epithelial cells, wherein the medium D comprises taurine, hydrocortisone and triiodo-thyronine; (j) culturing the non-adherent suspension embryoid bodies of step (a) in the medium B for 8-10 days; and (k) culturing the non-adherent suspension embryoid bodies of step (j) in the medium C for 8-12 weeks for formation of 3D retinal organoids, wherein the method is a unified method for producing multiple cell types of retina.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

FIGS. 6A-6D depicts quantification of RPE cells with respect to gene expression profile and biomarkers, in accordance with an embodiment of the present disclosure.

Figure 7:
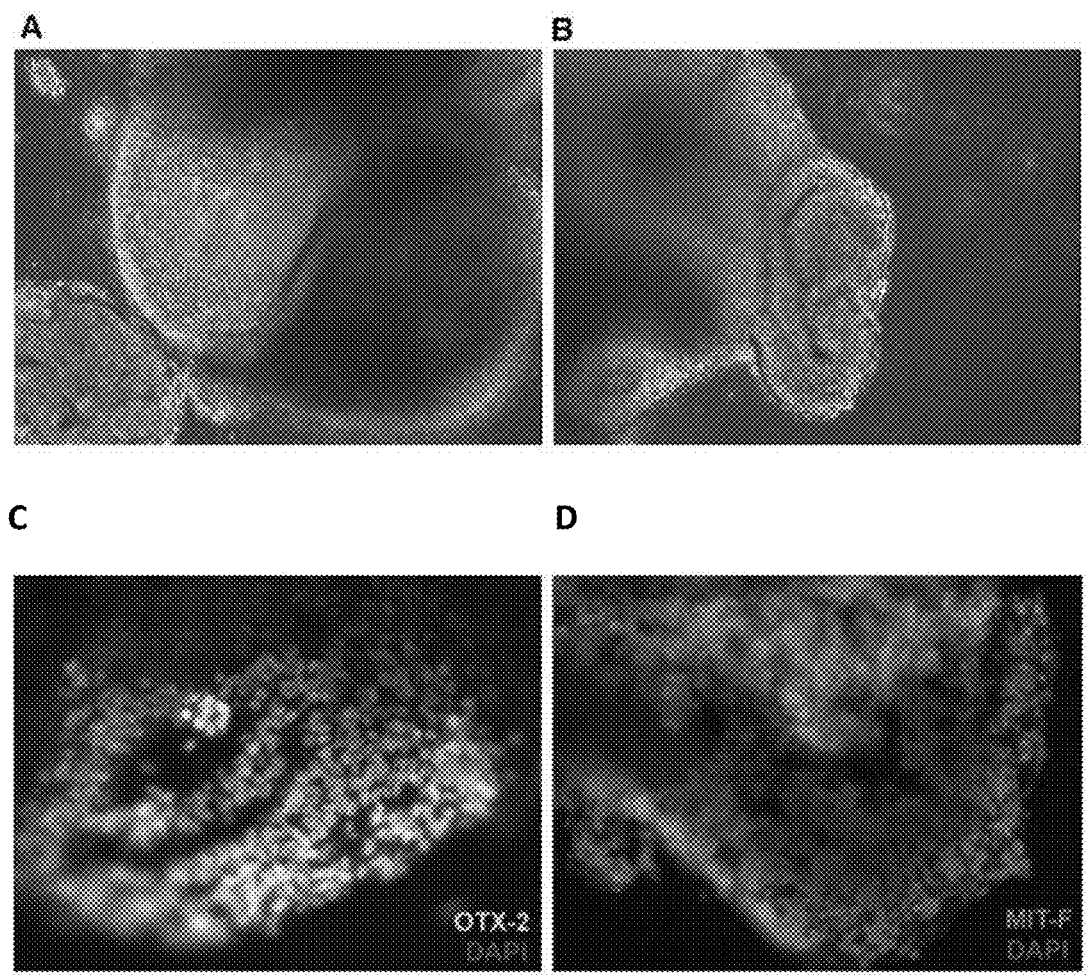

FIGS. 7A and 7B display phase contrast images of organoids at day 60, FIGS. 7C and 7D displays immunostaining of 10 μm sections of 3D retinal organoid for PR marker and RPE marker, in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Pluripotent stem cells are stem cells that has the potential to differentiate into any of the three germ layers: endoderm, mesoderm or ectoderm.

Xenofree refers to products that do not contain any animal derived component.

Retinal Pigmented Epithelium (RPE) is the pigmented cell layer just outside the neurosensory retina that nourishes retinal visual cells.

Photoreceptor cell is a specialized cell found in the retina. The cells are responsible for visual phototransduction.

Adherent cells are the cells that are anchorage dependent and have to be cultured on a suitable substrate that is specifically treated to promote cell adhesion and growth.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

ABBREVIATIONS

1. EDTA: Ethylenediaminetetraacetic acid
2. DMEM/F12: Dulbecco's Modified Eagle's medium/F12
3. ALK: Anaplastic lymphoma kinase
4. ROCK1: Rho Kinase
5. WNT: wingless-type MMTV
6. IGF: insulin like growth factor
7. VTN: Vitronectin
8. MEM/alpha: Modified Eagle's medium alpha
9. KOSR: Knockout serum
10. NEAA: Non-essential amino acids
11. ELISA: Enzyme linked immunosorbent assay
12. DPBS: Dulbecco's phosphate-buffered saline
13. WNT: Refers to Wnt signalling pathway
14. NOTCH: Refers to Notch signalling pathway Retinal degenerative diseases are caused due to deterioration of retinal cells and tissues and leads to progressive and eventual death of the cells of retina. Depending upon the severity of the disease it can result in varying degrees of irreversible vision loss. Currently there are millions of people worldwide who are suffering from different retinal degenerative disorders. One of the most common retinal degenerative diseases in terms of its occurrence worldwide is macular degeneration or age related macular degeneration. Macula is the part of the eye that helps in fine-tuning the details and is responsible for the central vision. Degeneration of the macula results in blurred or no vision in the centre of the visual field. There are supplements and medicaments, which are available for slowing down the progression of the disease, however they are not effective for preventing the disorder. Stem cell or retinal cell transplants have emerged as an effective therapy against the degenerative diseases. Advancements in the field have led to embryonic stem cell trials using human stem cell derived RPEs (Schwartz et al. Lancet. 2012. 25; 379(9817): 713-20).

The major limitation in the cell transplant based therapy is generation of retinal cells in a cost effective and efficient manner. Various protocols and methods have been explored for producing retinal cells such as photoreceptors, and retinal pigment epithelial cells. However, most of these methods are constrained by time and efficiency limitation.

The present disclosure provides with a method for generating multiple cell types of retina by differentiating induced pluripotent stem cells (iPSCs). The disclosure reveals a unified method, which can be employed for production of photoreceptors, retinal pigmented epithelial cells and 3D retinal organoids from a single source of pluripotent stem cells. The protocol describes generation of suspension embryoid bodies from iPSCs which can further be grown under specified and optimized conditions for generation of photoreceptors, retinal pigmented epithelial cells and 3D retinal organoids. The protocol as described in the present disclosure also discloses generation of adherent cultures from iPSCs which can further be grown under specified and optimized conditions for generation of photoreceptors, retinal pigmented epithelial cells and 3D retinal organoids. The protocol employs media compositions comprising growth factors, inducers and inhibitors that lead to differentiation of embryoid bodies into desired cell types.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a method for producing multiple cell types of retina from pluripotent stem cells, said method comprising: (a) generating non-adherent suspension embryoid bodies from the pluripotent stem cells in a medium A, wherein the medium A comprises growth factors, organic molecules, and lipid concentrates; (b) culturing the non-adherent suspension embryoid bodies in a medium B for 3-5 days, wherein the medium B comprises at least one WNT pathway inhibitor and at least one ALK receptor inhibitor; (c) culturing the embryoid bodies of step (b) on plates coated with at least one suitable extracellular matrix in the medium B for 4-7 days; (d) culturing the embryoid bodies of step (c) in a medium C for 5-10 days to form neural rosette like structures and epithelial like retinal progenitor cells, wherein the medium C does not comprise any inhibitor; (e) selecting the neural rosette like structures using a selection reagent, wherein the selection reagent allows preferential isolation and enrichment of the neural rosette like structures; (f) culturing the neural rosette like structures of step (e) on plates coated with at least one suitable extracellular matrix in a modified medium C until confluence for formation of photoreceptor progenitors, wherein the modified medium C comprises at least one ROCK inhibitor and at least one NOTCH inhibitor; (g) culturing the photoreceptor progenitors in the modified medium C for 8-12 weeks to form mature photoreceptor cells; (h) selecting and culturing the epithelial like retinal progenitor cells obtained in step (d) in the medium C for 5-7 days for formation of retinal pigmented epithelial progenitors; (i) culturing the retinal pigmented epithelial progenitors of step (h) in a medium D for 8-10 days to obtain mature retinal pigmented epithelial cells, wherein the medium D comprises taurine, hydrocortisone and triido-thyronine; (j) culturing the non-adherent suspension embryoid bodies of step (a) in the medium B for 8-10 days; and (k) culturing the non-adherent suspension embryoid bodies of step (j) in the medium C for 8-12 weeks for formation of 3D retinal organoids, wherein the method is a unified method for producing multiple cell types of the retina, to obtain multiple cell types of retina from pluripotent stem cells.

In an embodiment of the present disclosure, there is provided a method for producing multiple cell types of retina from pluripotent stem cells, said method comprising: (a) obtaining adherent cultures by direct differentiation from the pluripotent stem cells in a medium A, wherein the medium A comprises growth factors, organic molecules, and lipid concentrates; (b) culturing the adherent cultures in a medium B for 3-5 days, wherein the medium B comprises at least one WNT pathway inhibitor and at least one ALK receptor inhibitor; (c) culturing the adherent cultures of step (b) on plates coated with at least one suitable extracellular matrix in the medium B for 4-7 days; (d) culturing the adherent cultures of step (c) in a medium C for 5-20 days to form neural rosette like structures and epithelial like retinal progenitor cells, wherein the medium C does not comprise any inhibitor; (e) selecting the neural rosette like structures using a selection reagent, wherein the selection reagent allows preferential isolation and enrichment of the neural rosette like structures; (f) culturing the neural rosette like structures of step (e) on plates coated with at least one suitable extracellular matrix in a modified medium C until confluence for formation of photoreceptor progenitors, wherein the modified medium C comprises at least one ROCK inhibitor, and at least one NOTCH inhibitor; (g) culturing the photoreceptor progenitors in the modified medium C for 8-12 weeks to form mature photoreceptor cells; (h) selecting and culturing the epithelial like retinal progenitor cells obtained in step (d) in the medium C for 5-7 days for formation of retinal pigmented epithelial progenitors; (i) culturing the retinal pigmented epithelial progenitors of step (h) in a medium D for 8-10 days to obtain mature retinal pigmented epithelial cells, wherein the medium D comprises taurine, hydrocortisone and triido-thyronine, to obtain multiple cell types of retina from pluripotent stem cells.

In an embodiment of the present disclosure, there is provided a method for producing multiple cell types of retina from pluripotent stem cells as described herein, wherein selecting the neural rosette like structures is alternatively done by manual picking.

In an embodiment of the present disclosure, there is provided a method for producing multiple cell types of retina from pluripotent stem cells as described herein, wherein the multiple cell types of retina comprise photoreceptor cells, retinal pigmented epithelial cells and 3D retinal organoids.

In an embodiment of the present disclosure, there is provided a method for producing multiple cell types of retina from pluripotent stem cells as described herein, wherein the pluripotent stem cells are induced pluripotent stem cells.

In an embodiment of the present disclosure, there is provided a method for producing multiple cell types of retina from pluripotent stem cells as described herein, wherein generating the non-adherent suspension embryoid bodies from the pluripotent stem cell comprises: (a) growing the pluripotent stem cells on a plate coated with at least one suitable extracellular matrix in a medium A until confluence, wherein the medium A comprises growth factors, organic molecules and lipid concentrates; (b) dislodging the pluripotent stem cells of step (a) using a cell detachment enzyme solution to obtain detached pluripotent stem cells; (c) neutralizing the detached pluripotent stem cells with a neutralization medium to obtain neutralized pluripotent stem cell, wherein the neutralization medium comprises 5%-20% KOSR or a suitable neutralizing agent; and (d) seeding the neutralized pluripotent stem cells on a non-adherent suspension culture plate in a modified medium A for generating the non-adherent suspension embryoid bodies, wherein the modified medium A comprises at least one ROCK inhibitor. In another embodiment, the non-adherent suspension embryoid bodies generated in step (d) is further maintained in the modified medium A for 24-48 hour.

In an embodiment of the present disclosure, there is provided a method for producing multiple cell types of retina from pluripotent stem cells as described herein, wherein generating the adherent cell comprises: (a) growing the pluripotent stem cells on a plate coated with at least one suitable extracellular matrix in a medium A until confluence, wherein the medium A comprises growth factors, organic molecules and lipid concentrates.

In an embodiment of the present disclosure, there is provided a method for producing multiple cell types of retina from pluripotent stem cells as described herein, wherein the mature retinal pigmented epithelial cells obtained in step (i) is further passaged, comprising: (a) incubating the retinal pigmented epithelial cells with 0.05%-0.5% trypsin EDTA solution for detachment of non-pigmented and non-retinal pigmented epithelial cells for 2-10 minutes; (b) discarding the non-pigmented and non-retinal pigmented epithelial cells to obtain a pure population of retinal pigmented epithelial cells; (c) incubating the pure population of retinal pigmented epithelial cells with medium E, wherein the medium E comprises accutase enzyme and 0.2-0.5% trypsin EDTA; (d) neutralizing the pure population of retinal pigmented epithelial cells of step (c) using neutralization medium comprising 5-20% KOSR; and (e) culturing the neutralized pure population of retinal pigmented cells on a plate coated with at least one suitable extracellular matrix in the medium D. In another embodiment of the present disclosure, the retinal pigmented cells are alternatively incubated in medium E, wherein the medium E alternatively comprises at least one substance selected from a group consisting of collagenase enzyme, accustase, TrypLE Express, TrypLE Select, and compositions thereof, and wherein the neutralization medium alternatively comprises any suitable neutralizing agent well known in the art. In yet another embodiment of the present disclosure, wherein detachment of non-pigmented and non-retinal pigmented epithelial cells is done by manual selection under stereomicroscope.

In an embodiment of the present disclosure, there is provided a method for producing multiple cell types of retina from pluripotent stem cells as described herein, wherein the at least one WNT inhibitor is selected from the group consisting of 4-(1,3,3a,4,7,7a-Hexahydro-1,3-dioxo-4,7-methano-2H-isoindol-2-yl)-N-8-quinolinyl-Benzamide, 5-(Phenylsulfonyl)-N-piperidin-4-yl-2-(trifluoromethyl) benzene sulfonamide, 2-(2',3-Dimethyl-[2,4'-bipyridin]-5-yl)-N-(5-(pyrazin-2-yl)pyridin-2-yl) acetamide, 2-(4-(2-methylpyridin-4-yl)phenyl)-N-(4-(pyridin-3-yl)phenyl)

acetamide, 8-Tetrahydro-2-[4-(trifluoromethyl)phenyl]-4H-thiopyrano[4,3-d]pyrimidin-4-one, and combinations thereof.

In an embodiment of the present disclosure, there is provided a method for producing multiple cell types of retina from pluripotent stem cells as described herein, wherein the at least one WNT inhibitor is 4-(1,3,3a,4,7,7a-Hexahydro-1,3-dioxo-4,7-methano-2H-isoindol-2-yl)-N-8-quinolinyl-Benzamide.

In an embodiment of the present disclosure, there is provided a method for producing multiple cell types of retina from pluripotent stem cells as described herein, wherein the at least one ALK receptor inhibitor is selected from the group consisting of 4-[4-(1,3-benzodioxol-5-yl)-5-pyridin-2-yl-1H-imidazol-2-yl] benzamide, 4-(6-(4-(piperazin-1-yl)phenyl)pyrazolo[1,5-a]pyrimidin-3-yl)quinoline, 3-[(1R)-1-(2,6-dichloro-3-fluorophenyl)ethoxy]-5-(1-piperidin-4-ylpyrazol-4-yl)pyridin-2-amine, 5-chloro-2-N-[2-methoxy-4-[4-(4-methylpiperazin-1-yl)piperidin-1-yl]phenyl]-4-N-(2-propan-2-ylsulfonylphenyl)pyrimidine-2,4-diamine, and 9-ethyl-6,6-dimethyl-8-(4-morpholin-4-ylpiperidin-1-yl)-11-oxo-5H-benzo[b]carbazole-3-carbonitrile, 5-chloro-2-N-(5- methyl-4-piperidin-4-yl-2-propan-2-yloxyphenyl)-4-N-(2-propan-2-ylsulfonylphenyl) pyrimidine-2,4-diamine, and combinations thereof.

In an embodiment of the present disclosure, there is provided a method for producing multiple cell types of retina from pluripotent stem cells as described herein, wherein the at least one ALK receptor inhibitor is either 4-[4-(1,3-benzodioxol-5-yl)-5-pyridin-2-yl-1H-imidazol-2-yl] benzamide or 4-(6-(4-piperazin-1-yl)phenyl) pyrazolo[1,5-a]pyrimidin-3-yl)quinoline. In another embodiment, the at least one ALK inhibitor is a combination of 4-[4-(1,3-benzodioxol-5-yl)-5-pyridin-2-yl-1H-imidazol-2-yl] benzamide and 4-(6-(4-(piperazin-1-yl) phenyl) pyrazolo[1,5-a] pyrimidin-3-yl)quinoline.

In an embodiment of the present disclosure, there is provided a method for producing multiple cell types of retina from pluripotent stem cells as described herein, wherein the at least one NOTCH inhibitor is selected from a group consisting of N—[N-(3,5-Difluorophenacetyl)-L-alanyl]-S-phenylglycine t-butyl ester (DAPT), N-[cis-4-[(4-Chlorophenyl)sulfonyl]-4-(2,5-difluorophenyl)cyclohexyl]-1,1,1-trifluoromethanesulfonamide, 2-[(1R)-1-[[(4-Chlorophenyl)sulfonyl](2,5-difluorophenyl)amino]ethyl-5-fluorobenzenebutanoic acid, 5-Chloro-N-[(1S)-3,3,3-trifluoro-1-(hydroxymethyl)-2-(trifluoromethyl)propyl]-2-thiophenesulfonamide, N-[(1S)-2-[[(7S)-6,7-Dihydro-5-methyl-6-oxo-5H-dibenz[b,d]azepin-7-yl]amino]-1-methyl-2-oxoethyl]-3,5- difluorobenzeneacetamide, (R)-2-Fluoro-α-methyl[1,1'-biphenyl]-4-acetic acid, N-[(1S)-2-[[(3S)-2,3-Dihydro-1-methyl-2-oxo-5-phenyl-1H-1,4-benzodiazepin-3-yl]amino]-1-methyl-2-oxoethyl]-3,5-difluorobenzeneacetamide, 3,5-Bis(4-nitrophenoxy)benzoic acid, (5S)-(tert-Butoxycarbonylamino)-6-phenyl-(4R)-hydroxy-(2R)-benzylhexanoyl)-L-leucy-L-phenylalaninamide, 7-Amino-4-chloro-3-methoxy-1H-2- benzopyran, (2S)—N-[(3,5-Difluorophenyl)acetyl]-L-alanyl-2-phenyl] glycine 1,1-dimethylethyl ester, and combinations thereof. In another embodiment of the present disclosure, the at least NOTCH inhibitor is N—[N-(3,5-Difluorophenacetyl)-L-alanyl]-S-phenylglycine t-butyl ester (DAPT).

In an embodiment of the present disclosure, there is provided a method for producing multiple cell types of retina from pluripotent stem cells as described herein, wherein the at least one suitable extracellular matrix is selected from the group consisting of laminin, vitronectin, fibronectin, collagen, poly-L-lysine, poly-L-ornithine, and combinations thereof. In another embodiment, the at least one suitable extracellular matrix is vitronectin.

In an embodiment of the present disclosure, there is provided a method for producing multiple cell types of retina from pluripotent stem cells as described herein, wherein the at least one suitable extracellular matrix is xenofree.

In an embodiment of the present disclosure, there is provided a method for producing multiple cell types of retina from pluripotent stem cells as described herein, wherein the medium C further comprises DMEM/F12, KOSR, and NEAA.

In an embodiment of the present disclosure, there is provided a method for producing multiple cell types of retina from pluripotent stem cells as described herein, wherein the at least one ROCK inhibitor is selected from the group consisting of 4-[(1R)-1-aminoethyl]-N-pyridin-4-yl-cyclohexane-1-carboxamide, 4-[(1R)-1-aminoethyl]-N-(1H-pyrrolo[2,3-b] pyridin-4-yl)benzamide, 6-aminochromen-4-one, 5-(1,4-diazepan-1-ylsulfonyl) isoquinoline, 4-methyl-5-[[(2S)-2-methyl-1,4-diazepan-1-yl]sulfonyl]isoquinoline, and combinations thereof.

In an embodiment of the present disclosure, there is provided a method for producing multiple cell types of retina from pluripotent stem cells as described herein, wherein the at least one ROCK inhibitor is 4-[(1R)-1-aminoethyl]-N-pyridin-4-ylcyclohexane-1-carboxamide.

In an embodiment of the present disclosure, there is provided photoreceptor cells produced from the method as described herein.

In an embodiment of the present disclosure, there is provided retinal pigmented epithelial cells produced from the method as described herein.

In an embodiment of the present disclosure, there is provided 3D retinal organoids produced from the method as described herein.

In an embodiment of the present disclosure, there is provided 3D optic cups produced from the method as described herein.

In an embodiment of the present disclosure, there is provided a pharmaceutical composition comprising the photoreceptor cells produced from the method as described herein.

In an embodiment of the present disclosure, there is provided a pharmaceutical composition comprising the retinal pigmented epithelial cells produced from the method as described herein.

In an embodiment of the present disclosure, there is provided a pharmaceutical composition comprising the 3D retinal organoids produced from the method as described herein.

In an embodiment of the present disclosure, there is provided a pharmaceutical composition comprising the photoreceptor cells produced from the method as described herein, wherein the composition is used in manufacture of a medicament.

In an embodiment of the present disclosure, there is provided a pharmaceutical composition comprising the retinal pigmented epithelial cells produced from the method as described herein, wherein the composition is used in manufacture of a medicament.

In an embodiment of the present disclosure, there is provided a pharmaceutical composition comprising the 3D retinal organoids produced from the method as described herein, wherein the composition is used in manufacture of a medicament.

In an embodiment of the present disclosure, there is provided a pharmaceutical composition comprising the photoreceptor cells produced from the method as described herein, wherein the composition is used in manufacture of a medicament, and wherein the medicament is used for treatment of retinal degenerative diseases.

In an embodiment of the present disclosure, there is provided a pharmaceutical composition comprising the retinal pigmented epithelial cells produced from the method as described herein, wherein the composition is used in manufacture of a medicament, and wherein the medicament is used for treatment of retinal degenerative diseases.

In an embodiment of the present disclosure, there is provided a pharmaceutical composition comprising the 3D retinal organoids produced from the method as described herein, wherein the composition is used in manufacture of medicament, and wherein the medicament is used for treatment of retinal degenerative diseases.

In an embodiment of the present disclosure, there is provided a pharmaceutical composition comprising the photoreceptor cells produced from the method as described herein, wherein the composition is used in manufacture of a medicament, and wherein the medicament is used for treatment of retinal degenerative diseases selected from the group consisting of retinitis pigmentosa, Best disease, Stargardt disease, Usher syndrome, rod-cone dystrophy, and age related macular degeneration.

In an embodiment of the present disclosure, there is provided a pharmaceutical composition comprising the retinal pigmented epithelial cells produced from the method as described herein, wherein the composition is used in manufacture of a medicament, and wherein the medicament is used for treatment of retinal degenerative diseases selected from the group consisting of retinitis pigmentosa, Best disease, Stargardt disease, Usher syndrome, rod-cone dystrophy, and age related macular degeneration.

In an embodiment of the present disclosure, there is provided pharmaceutical composition comprising the 3D retinal organoids produced from the method as described herein, wherein the composition is used in manufacture of a medicament, and wherein the medicament is used for treatment of retinal degenerative diseases selected from the group consisting of retinitis pigmentosa, Best disease, Stargardt disease, Usher syndrome, rod-cone dystrophy, and age related macular degeneration.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

The examples below describe the protocol disclosed in the present invention in detail. The protocol focuses on the differentiation of induced pluripotent stem cell, to form multiple cell types of retina. However, it should be noted that the present protocol can be used for differentiating other pluripotent stem cells as well, such as, embryonic stem cells. Apart from providing with a unified protocol for generating multiple cell types of retina, the protocol also provides with method for generating suspension type embryoid bodies from pluripotent stem cell. The suspension type embryoid bodies are further cultured under specific and optimized media and incubation conditions for formation of retinal cells such as photoreceptors and RPEs.

The cells obtained from the protocol were further verified by using immunofluorescence and RT-PCR technique. The cells display expression of important and relevant markers with respect to the days of differentiation. The features that differentiate the current protocols from other similar cell culture protocols include the media composition, number of days required for cell differentiation, selection of neural rosette like structures using non-enzyme based selection reagent or manual picking of rosette like structures, which allows preferential isolation and enrichment of the neural rosettes.

Materials and Methods

Composition of the different media as used in the protocol is described below:

Composition of Medium A—Medium A refers to mTESR medium procured form Stem Cell Technologies or Stemflex or E8 medium procured from ThermoFisher Scientific. Modified medium A has an additional supplementary component as compound 4-[(1R)-1-aminoethyl]-N-pyridin-4-ylcyclohexane-1-carboxamide (Y27632).

Composition of Medium B—Medium B here refers to Differentiation Induction Medium (DIM) having composition as below:

TABLE 1

| Components | For 50 ml | Final concentration |
| --- | --- | --- |
| DMEM/F12 | 42.5 ml | 10% |
| KOSR | 5 ml | 1% |
| Sodium pyruvate | 0.5 ml | 1% |
| Sodium bicarbonate | 0.5 ml | 1% |
| HEPES buffer | 0.5 ml | 1% |
| Non-essential amino acids | 0.5 ml | 1% |
| N1 media supplements | 0.5 ml | 1X |
| Compound 1 (2 mM)* | 50 µl | 2 µM |
| Compound 2 (10 mM)* | 50 µl | 10 µM |
| Compound 3 (1 mM)* | 5 µl | 100 nM |
| IGF1 (100 ng/ml) | 5 µl | 10 ng/ml |
| Activin A | 10 µl | 10 µg/ml |
| Nicotinamide | 5 µl | 10 mM |

*Compound1: 4-(1,3,3a,4,7,7a-Hexahydro-1,3-dioxo-4,7-methano-2H-isoindol-2-yl)-N-8-quinolinyl-Benzamide (WNT pathway inhibitor)

Compound 2: 4-[4-(1,3-benzodioxol-5-yl)-5-pyridin-2-yl-1H-imidazol-2-yl]benzamide (ALK receptor inhibitor)
Compound 3: 4-(6-(4-(piperazin-1-yl)phenyl)pyrazolo[1,5-a]pyrimidin-3-yl)quinoline (ALK receptor inhibitor)

Composition of Medium C: Medium C here refers to differentiation propagation medium (DPM) having composition as below:

TABLE 2

| Components | For 50 ml | Final Concentration |
| --- | --- | --- |
| DMEM/F12 | 47 ml | |
| Knock-Out Serum Replacement (KOSR) | 0.5 ml | 1% |
| Sodium pyruvate | 0.5 ml | 1% |
| Sodium bicarbonate | 0.5 ml | 1% |

TABLE 2-continued

| Components | For 50 ml | Final Concentration |
|---|---|---|
| HEPES buffer | 0.5 ml | 1% |
| Non-essential amino acids | 0.5 ml | 1% |
| N1 media supplement (100X) | 0.5 ml | 1X |

Modified Medium C has an additional component as compound 4-[(1R)-1-aminoethyl]-N-pyridin-4-ylcyclohexane-1-carboxamide (Y27632), N—[N-(3,5- Difluorophenacetyl)-L-alanyl]-S-phenylglycine t-butyl ester (DAPT), a NOTCH pathway inhibitor as Compound 5 and 3-[4-Methyl-2-(2-oxo-1,2-dihydro-indol-3-ylidenemethyl)-1H-pyrrol-3-yl]-propionic acid (SU5402), a FGFR antagonist as Compound 6.

Table 3 as mentioned below refers to Medium D (RPE maturation medium):

TABLE 3

| Components | For 50 ml | Final Concentration |
|---|---|---|
| MEMα modified | 46.5 ml | |
| KOSR | 2.5 ml | 5% |
| Glutamax | 0.5 ml | 1% |
| Taurine (50 mg/ml) | 0.25 ml | 0.25 mg/ml |
| Hydrocortisone (20 mg/ml) | 25 μl | 10 μg/ml |
| Triido-Thyronine (2 mg/ml) | 1 μl | 0.0065 μg/ml |
| Ni media supplement (100X) | 0.5 ml | 1X |

The neutralization medium used in the present study is DMEM/F12 (GIBCO) supplemented with 10% KOSR or a suitable neutralization agent.

The selection reagent used in the present study is Stem Diff Neural rosette selection reagent from Stem Cell Technologies.

Table 4 below provides different reagents and the vendors they were procured from:

TABLE 4

| Chemicals | Company | Catalog No |
|---|---|---|
| Vitronectin | ThermoFisher | A14700 |
| DMEM/F12 | GIBCO | 10565-018 |
| DPBS | GIBCO | 14190-136 |
| Knock out serum (KOSR) | GIBCO | 10828-028 |
| HEPES buffer | GIBCO | 15630-080 |
| Non-essential Amino acids | GIBCO | 11140-050 |
| Accutase | GIBCO | A11105-01 |
| Penicillin Streptomycin | GIBCO | 15140-122 |
| Trypsin EDTA | GIBCO | 25200-072 |
| Cryostor CS10 | Stem technologies | 7931 |
| IWR1 (compound 1) | Sigma | I0161-25 MG |
| N1 supplement | Sigma | N6530-5 ML |
| IGF-1 | Stem lltechnologies | 78022 |
| Stemflex | ThermoFisher | A3349401 |
| Y27632 (ROCK 1 inhibitor) | Stem cell technologies | 72302 |
| LDN193189 (compound 2) | Stem cell technologies | 72142 |
| SB431542 (compound 3) | Stem cell technologies | 72234 |
| Sodium bicarbonate | Thermo Fisher | 25080-060 |
| Sodium pyruvate | Thermo Fisher | 11360-070 |
| Y-27632 (ROCK inhibitor) | Tocris | 1254 |
| DAPT (NOTCH inhibitor, compound 5) | Sigma | D5942 |
| SU5402 (FGFR antagonist, compound 6) | Sigma | SML0443 |

TABLE 4-continued

| Chemicals | Company | Catalog No |
|---|---|---|
| Activin A | ThermoFisher | PHG9014 |
| Nicotinamide | Sigma | 72340 |
| TrypLE Select | ThermoFisher | 12563011 |

Differentiation Protocol in Detail:

Example 1

Generation of embryoid bodies: (a) Vitronectin was resuspended in DPBS at 1-5%, added to tissue culture plates and incubated overnight to obtain Vitronectin (VTN) coated plates. iPSCs for the present study were obtained from the umbilical cord blood of humans. Lymphocytes were isolated from the blood and reprogrammed into iPSCs using transcription factors such as Oct4, Sox-2, KLF4 and cMYC via episomal vectors (non-integrative). The NcGMP1 induced pluripotent stem cells (iPSC) were then grown on the VTN coated plates in medium A and passaged regularly (passaging ratio 1:5-1:6) upon 80-90% confluency: (b) On attaining about 80% confluence, the cells were treated with prewarmed dissociation enzyme (accutase) at 1 ml/10 $cm^2$ and placed in incubator for 3 minutes. The enzyme was neutralized with 3 times (v:v) 10% KOSR containing Medium D (here refers to RPE maturation DMEM-high glucose media), and the dissociated cells were gently transferred to 15 ml Falcon tube using 2 ml serological pipette avoiding dissociation of the iPSC colonies; (c) the cells were centrifuged at 800 g for 2 mins to form a cell pellet. After aspirating the spent media, the cell pellet was mildly dislodged (careful so as to avoid making single cells) and seeded onto non-adherent suspension culture plates forming forced aggregates of embryoid bodies (EB) in modified medium A. For non-adherent culture based retinal differentiation the iPSCs were allowed to grow under static culture conditions. The cells were maintained in modified medium A for 24-48 hours with media change within 24-hour interval; (d) The EBs or adherent cultures were then shifted gradually to medium B in suspension and media was changed every day for 3-5 days. EBs were then further used for generation of photoreceptor cells, retinal pigmented epithelial cells and 3D retinal organoids, while only photoreceptor cells and retinal pigmented cells can be generated with adherent cells.

Example 2

Generation of 3D organoids from EBs: The suspension type EBs of step (d) in Example 1 were grown for another 7 days. Post 7 days, EBs were then transferred in medium C and cultured as suspension for 12 weeks with alternate day media change to form 3D retinal organoids or 3D optic cups.

Example 3

Generation of photoreceptors: The suspension type EBs or adherent cultures of step (d) in Example 1 were transferred on 2% VTN (in medium B) coated tissue culture plates to form adherent EBs. The cells were cultured in modified medium B for 2 more days with media change every day. After 4-7 days, the cells were transferred to Medium C. Upon confluency between 5-10 days in Medium C, neural rosette like structures were selected using Stem Diff Neural rosette selection reagent. The neural rosette like structures were collected with or without dissociation using accutase enzyme. The cells were then plated on 2% VTN coated 12 well dish in modified Medium C and cultured till they attained confluency to obtain photoreceptor progenitors. The PR progenitors were further grown and expanded in Medium C and passaged for 12 weeks to obtain photoreceptor cells. Stock vials of PR cells can be prepared at desired day point for further studies.

Example 4

Generation of RPEs: The remaining cells (epithelial like retinal progenitor cells) that were left in the parent plate in Example 2, post selection of neural rosette like structures were re-plated and continued for 5-7 days in Medium C to form retinal pigmented epithelial progenitors.

The cells were then transferred to Medium D and grown for another 30 days to form matured retinal epithelial cells. Stock vials of matured RPE cells were prepared at desired day point for further studies.

Example 5

The RPE cells whenever confluent were split and passaged at 1:2 to 1:5 ratio by the following method:
a. 0.005-0.5% Trypsin-EDTA was added to the confluent cells and incubated at culture conditions for 5 mins.
b. Non-pigmented and non RPE cells would detach at this condition and the media with non-desired cell population was discarded.
c. Cells were replenished with TrypLE Select and or accutase and incubated at culture conditions for 5-10 mins.
d. Cells could also be picked manually under the stereomicroscope.
e. Colonies were scraped with cell lifter and clumps were dissociated in 10% KOSR media.
f. The dissociated cells were transferred in falcon tube and centrifuged at 800 g for 2 mins followed by replating on freshly coated VTN plates and further grown for few passages.

Example 6

Once the cells were produced using the above unified protocol, they were examined for expression of relevant markers.

Figure 1:
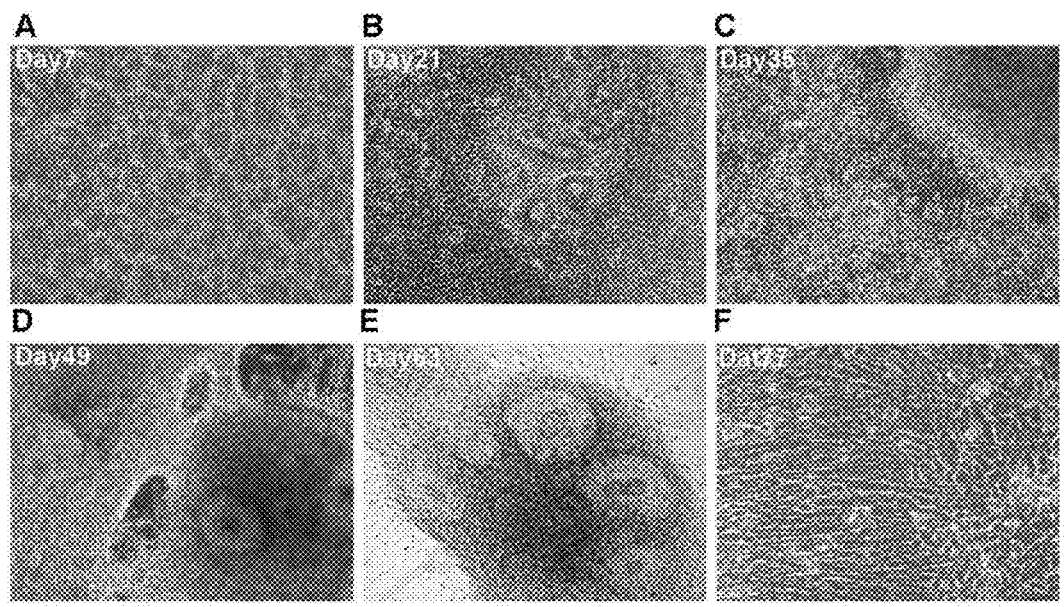
FIGS. 1A-1F shows phase contrast images displaying temporal changes in cellular morphology from undifferentiated iPSCs to photoreceptor-like cells, in accordance with an embodiment of the present disclosure.
Figure 2:
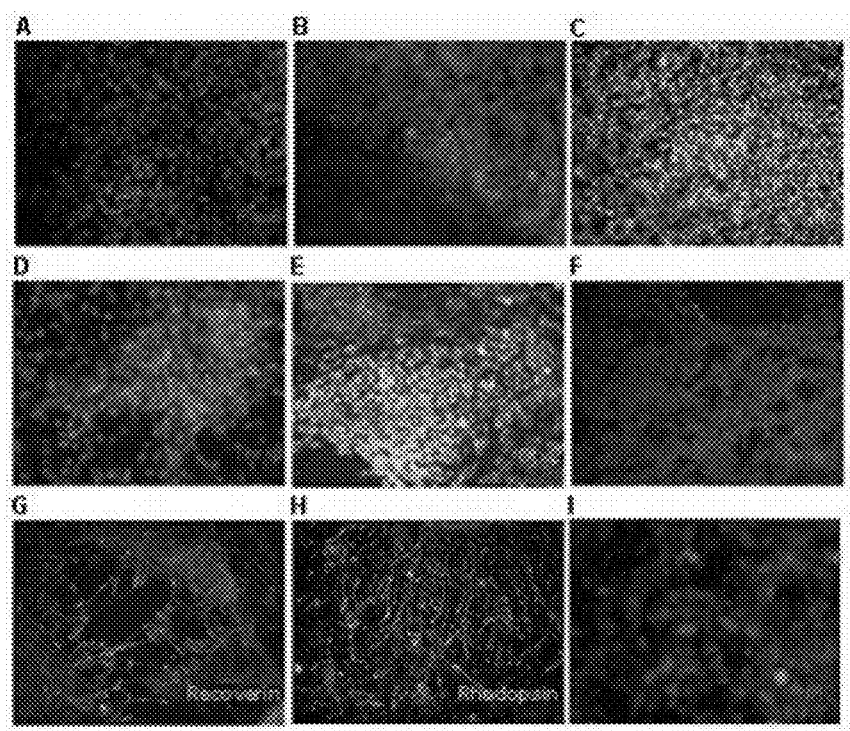
FIGS. 2A-2I depicts immunostaining of PR cells with different cell biomarkers, in accordance with an embodiment of the present disclosure.

Phase contrast microscopy: FIG. 1 depicts the phase contrast images of photoreceptor cells at different days throughout the differentiation. The images display temporal changes in cellular morphology from undifferentiated iPSCs to photoreceptor-like cells. The images are labelled as A) differentiation day 7, B) differentiation day 21, C) differentiation day 35, D) differentiation day 49, E) differentiation Day 63, and F) differentiation day 77. Gradual change in cells differentiating form iPSCs to PR cells can be observed.

FIG. 2A-2I depict the images of PR cells post staining with relevant antibodies. As can be observed from the images the cells display markers, A) Pax6, B) Sox2, C) RX, D) Thrβ, E) Otx2, F) BRN3, G) Recoverin, H) Rhodopsin, and I) Nrl2

Real Time PCR quantification: Gene expression profile during differentiation of PR cells was performed. For quantitative polymerase chain reaction (Q-PCR) analysis, RNA was extracted by RNeasy kit (Qiagen, Hilden, Germany, http://www.qiagen.com), and cDNA conversion was done using Revert Aid kit (Thermo Scientific) as per the manufacturer's instructions. 1 μg of RNA was used for cDNA conversion. Q-PCR was done with SYBER Green master mix (Life Technologies) using mRNA specific primers (sequences of primers as listed below as Table 5) on ABI 7900HT (Life Technologies) and was analysed by SDS 2.4 software.

Table 5 below lists out the sequences of the primers used in the present disclosure.

TABLE 5

| | | |
|---|---|---|
| hPAX6 F | 5'-AGTTCTTCGCAACCTGGCTA-3' | SEQ ID NO: 1 |
| hPAX6 R | 5'-TGGTATTCTCTCCCCCTCCT-3' | SEQ ID NO: 2 |
| hZO-1 F | 5'-TGAGGCAGCTCACATAATGC-3' | SEQ ID NO: 3 |
| hZO-1 R | 5'-GGGAGTTGGGGTTCATAGGT-3' | SEQ ID NO: 4 |
| hSIX3 F | 5'-CCGGAAGAGTTGTCCATGTT-3' | SEQ ID NO: 5 |
| hSIX3 R | 5'-CGACTCGTGTTTGTTGATGG-3' | SEQ ID NO: 6 |
| hLHX2 F | 5'-GCTCGGGACTTGGTTTATCA-3' | SEQ ID NO: 7 |
| hLHX2 R | 5'-GTTGAAGTGTGCGGGGTACT-3' | SEQ ID NO: 8 |
| hRX F | 5'-GAACAGCCCAAGAAAAAGCA-3' | SEQ ID NO: 9 |
| hRX R | 5'-GCTGTACACGTCCGGGTAGT-3' | SEQ ID NO: 10 |
| hMITF F | 5'-CCAGGCATGAACACACATTC-3' | SEQ ID NO: 11 |
| hMITF R | 5'-TCCATCAAGCCCAAGATTTC-3' | SEQ ID NO: 12 |
| hRPE65 F | 5'-GATCTCTGCTGCTGGAAAGG-3' | SEQ ID NO: 13 |
| hRPE65 R | 5'-TGGGGAGCGTGACTAAATTC-3' | SEQ ID NO: 14 |
| hBESTROPHI | 5'-GGCAGAACACAAGCAGTTGG-3' | SEQ ID NO: 15 |
| hBESTROPHI | 5'-ACGCAAGGTGTTCATCTCGT-3' | SEQ ID NO: 16 |
| hTYROSINAS | 5'-ACCCATTGGACATAACCGGG-3' | SEQ ID NO: 17 |
| hTYROSINAS | 5'-AGAGTCTGGGTCTGAATCTTGT-3' | SEQ ID NO: 18 |
| hEZRIN F | 5'-TCAATGTCCGAGTTACCACCA-3' | SEQ ID NO: 19 |
| hEZRIN R | 5'-GGCCAAAGTACCACACTTCC-3' | SEQ ID NO: 20 |
| hDCT F | 5'-GGTTCCTTTCTTCCCTCCAG-3' | SEQ ID NO: 21 |
| hDCT R | 5'-AACCAAAGCCACCAGTGTTC-3' | SEQ ID NO: 22 |

TABLE 5-continued

```
hNrl F       5'-ATG TGG ATT GGA CGA CTT C-3'       SEQ ID NO: 23
hNrl R       5'-TTG GCG AGA TTG TCT TGG-3'         SEQ ID NO: 24 hTRB2 F      5'-ACA GGA GAT TTC ATT CGG G-3'       SEQ ID NO: 25
hTRB2 R      5'-TTG TAA GAC TAT CAT CTG GGT G-3'   SEQ ID NO: 26 hBLIMP1 F    5'-GTG GTA TTG TCG GGA CTT TG-3'      SEQ ID NO: 27
hBLIMP1 R    5'-GGT TGC TTT AGA CTG CTC TG-3'      SEQ ID NO: 28 hCHX10 F     5'-CGA CAC AGG ACA ATC TTT ACC-3'     SEQ ID NO: 29
hCHX10 R     5'-CAT AGA CGT CTG GGT AGT GG-3'      SEQ ID NO: 30 hBRN3 F      5'-CTCGCTCGAAGCCTACTTTG-3'            SEQ ID NO: 31
hBRN3 R      5'-GACGCGCACCACGTTTTTC-3'             SEQ ID NO: 32 hSOX-2 F     5'-CCGCGTCAAGCGGCCCATGAA-3'           SEQ ID NO: 33
hSOX-2 R     5'-GCCGCTTCTCCGTCTCCGACAA-3'          SEQ ID NO: 34 hβ-actin F   5'-TCACCCACACTGTGCCCATCTACGA-3'       SEQ ID NO: 35
hβ-actin R   5'-CAGCGGAACCGCTCATTGCCAATGG-3'       SEQ ID NO: 36
```

Figure 3:
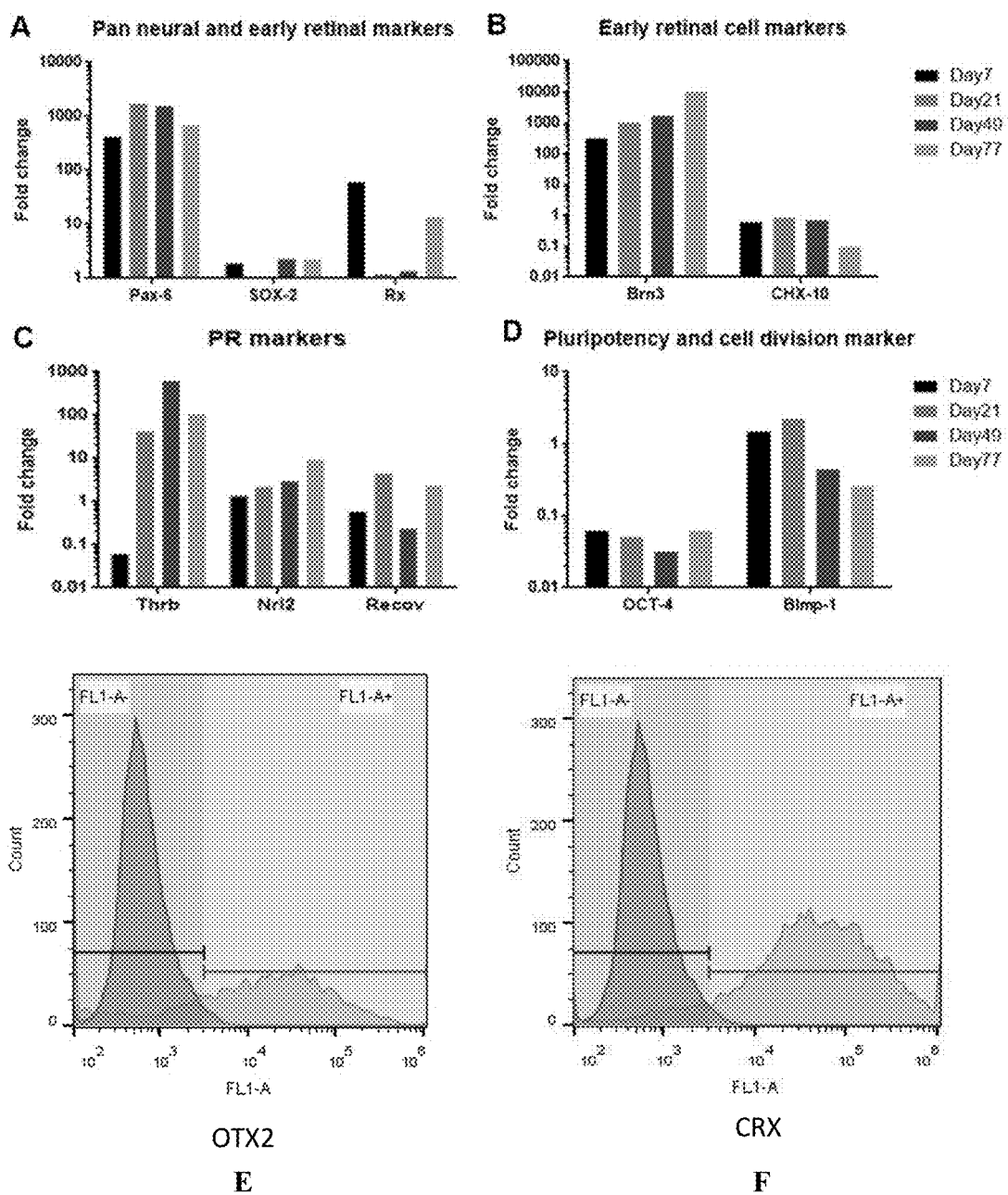
FIGS. 3A-3F depicts results of gene expression profile of different cell biomarkers of PR cells on differentiation days 7, 21, 49, and 77, in accordance with an embodiment of the present disclosure.

Normalization was performed based on the average of expression of constitutive gene β-actin. Study was performed for differentiation day 7, day 21, day 49 and day 77. The different genes analysed are as below:

(a) Pan neural markers Pax-6 and Sox-2 along with early retinal marker RX: FIG. 3A displays the graph depicting the gene expression profile for Pax-6. Sox-2 and RX.
Gradual increase in expression of genes can be observed from differentiation day 7 to day 77.

(b) Retinal ganglion transcription factors Brn3 and CHX10: FIG. 3B displays the graph depicting the gene expression profile for transcription factors Brn3 and CHX10. Enhancement in the expression of both the genes can be observed with increase in number of days of differentiation.

(c) Markers for rods and cones (PR cells): Cone photoreceptor transcription factor Thrβ, Rod photoreceptor specific transcription factor Nrl2 and photoreceptor marker recoverin were analysed and the results have been depicted in FIG. 3C. It is apparent from the figure that all the cell markers display an increase in expression with respect to increase in differentiation days.

(d) Pluripotency markers: Gene expression of pluripotency marker such as Oct4 and cell migration and division marker Blmp1 were also checked. As can be observed in FIG. 3D, both the genes displayed downregulation from day 7 day 77 of cell differentiation.

FIGS. 3E and 3F depict the quantification of PR cells based on the markers OTX2 and CRX, respectively.

Immunocytochemistry or Immunofluorescence study: For indirect immunofluorescence, cells were harvested at appropriate time points and fixed in 2% paraformaldehyde for 20 minutes at room temperature (RT) followed by washing three times in 1XPBS. Cells were then permeabilized for 5 minutes with 0.1% Triton X-100 (Sigma), then blocked for 1 hour at RT with 4% fetal bovine serum (FBS), and incubated with primary antibodies (list of antibodies as mentioned below in Table 6).

Followed by over-night primary antibody incubation at 48 hours, cells were washed with 1PBS twice and probed with secondary antibodies for 1 hour at room temperature After secondary antibody treatment cells were washed thoroughly with 1XPBS. For antibodies specific against membrane epitope cells were not permeabilized. Cell nuclei were counterstained with DAPI (4', 6-diamidino-2-phenylindole; 100 ng/ml) for 7 mins at RT and observed under fluorescent microscope (Olympus IX73).

Table 6 below depicts the list of antibodies used for the present study.

TABLE 6

| Vendor | CATALOG NO. | ANTIBODY NAME |
| --- | --- | --- |
| Abcam | ab80651 | Mouse monoclonal Nun |
| Abcam | ab13826 | Mouse monoclonal RPE65 |
| Abcam | ab738 | Mouse monoclonal Tyrosinase |
| Abcam | ab4069 | Mouse monoclonal Ezrin |
| Abcam | ab109290 | Rabbit monoclonal to SOX1 |
| Abcam | ab195045 | Rabbit monoclonal PAX6 |
| Santacruz | sc271889 | Mouse monoclonal Retinal RX |
| Abcam | ab31928 | Mouse monoclonal Recoverin |
| Abcam | ab81213 | Rabbit monoclonal BRN3A |
| Santacruz | sc-377138 | Mouse monoclonal CRX |
| Sigma | T7451 | Mouse monoclonal Acetylated Tubulin |
| Adipogen | AG-20B-0020-C100 | anti-Polyglutamylation Modification, mAb (GT335) |
| Abcam | ab221391 | Rabbit polyclonal NRL |
| Abcam | ab53170 | Rabbit polyclonal Thyroid Hormone |
| Abcam | ab16288 | Mouse monoclonal TRA-1-60 |
| Abcam | ab171380 | Mouse monoclonal SOX-2 |
| Abcam | ab18976 | Rabbit polyclonal Oct-4 |
| Santacruz | Sc-365519 | Mouse monoclonal CHX10 |
| Merck Millipore | ABE1402 | Rabbit polyclonal LHX2 |
| Merck Millipore | MAB5580 | Mouse monoclonal anti-arrestin, visual |
| Abcam | AB7260 | Rabbit polyclonal CFAP |

Figure 4:
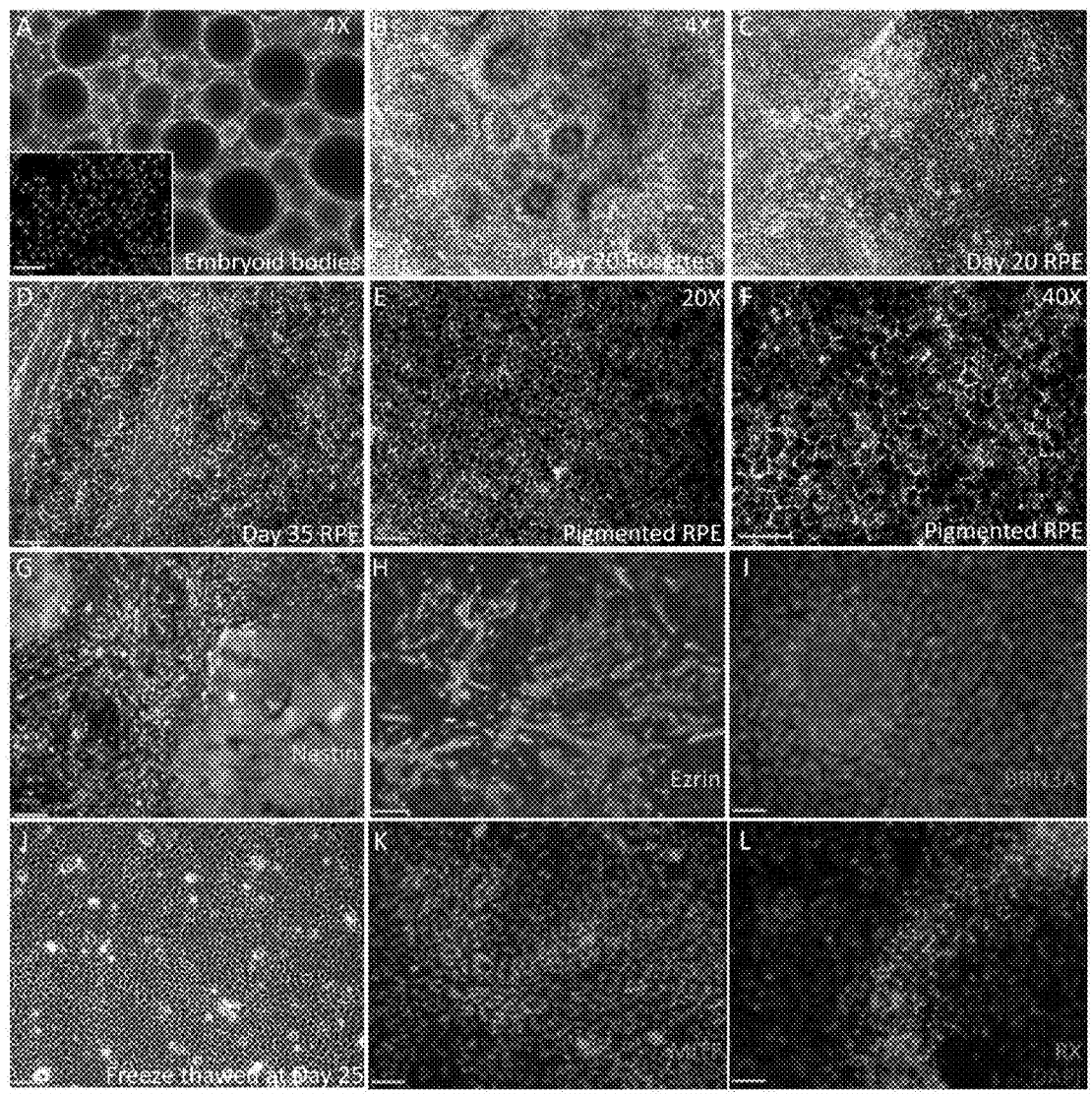
FIGS. 4A-4L depicts phase contrast microscopy and immunofluorescence analysis of RPE differentiation, in accordance with an embodiment of the present disclosure.

FIG. 4 depicts phase contrast analysis and immunofluorescence studies of differentiation of RPE from iPS cells. FIG. 4A represents day 2 of the embryoid bodies, and FIG. 4A inset represents Oct4 staining in NcGMP1 iPSC, FIGS. 4B, and 4C represents Day 20 rosette populations and FIG. 4D represents non-rosette populations. FIGS. 4E and F represents pigmented RPE after rosette selection, and FIGS. 4G-4I represent RPE like cells immunostained against Pax6, Nestin, Ezrin and BRN3A antibodies, respectively. FIG. 4J depicts Freeze thaw viability of RPE progenitors, and FIG. 4K-4L represents immunostaining against MITF and RX on freeze thawed cells. Scale bars represent 100 μm. Images unless mentioned are at 10× magnification.

Figure 5:
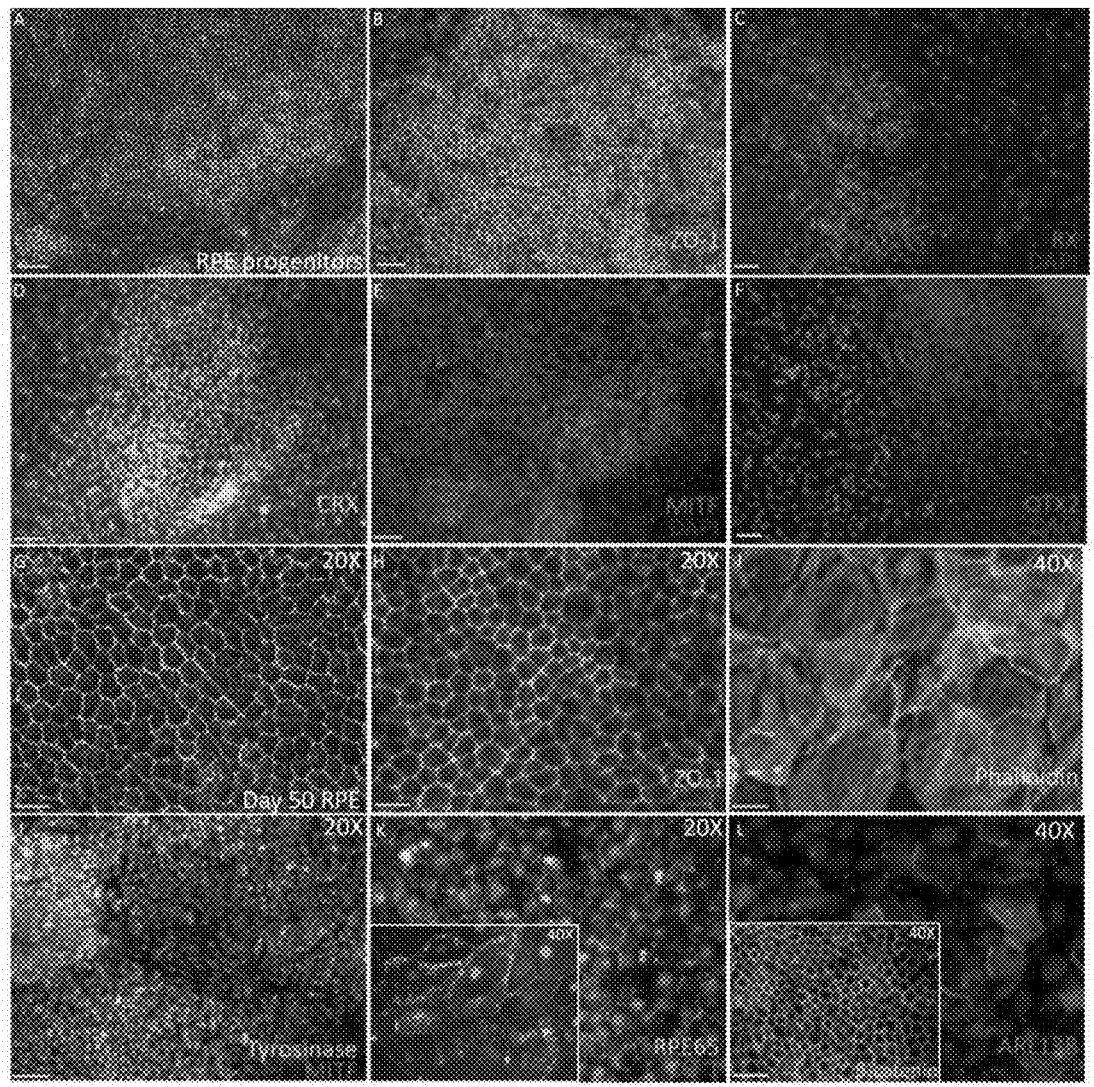
FIGS. 5A-5L depicts authentication of RPE by immunohistochemistry studies, in accordance with an embodiment of the present disclosure.

FIG. 5 depicts characterization of mature RPE by immunofluorescence analysis. Figures A and G represent purified mature RPE cells. FIGS. 5B and 5H represent immunostaining of RPE for ZO-1. FIGS. 5C-5F represent immunofluorescence images of transcription factors RX, CRX, MITF, and OTX2 respectively. FIG. 5I represent the staining of phalloidin. FIGS. 5J-5L represent immunostaining of mature RPE specific markers like Tyrosinase, RPE-65, ARL13B, β-catenin (inset) in pigmented cells. Scale bars represent 100 µm. Images depicted unless mentioned are at 10× magnification. The depicted images clearly represent the expression of appropriate markers and transcription factors expressed by RPE. Hence, establishing the validity of the protocol as disclosed in the present disclosure.

Figure 6D:
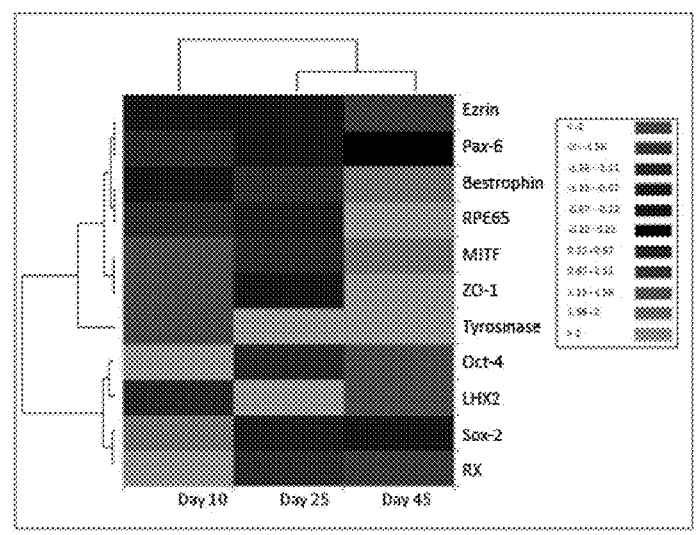

FIG. 6A-6B depicts RPE quantification by flow cytometry of MITF and RX in immature RPE respectively. Sandwich ELISA shows secretion of key growth factors from fully mature and pigmented RPE compared to positive and negative controls (FIG. 6C). FIG. 6D represents Real time PCR based quantification of key gene expression and it representation as heat map, respectively.

FIGS. 7A and 7B depict the phase contrast images of 3D retinal organoids at day 60. The images show 3D self-organized retinal tissue formation in suspension cultures.

FIGS. 7C and 7D depict the images post immunostaining of 3D retinal organoids. 10 µm section was taken and immunostained for PR marker A) OTX-2 and RPE marker B) MIT-F at day 25. FIG. 7C depicts OTX-2 and RPE marker and FIG. 7D depicts the presence of MIT-F which represents the presence of both RPE and PR in retinal organoid structures.

Advantages of the Present Disclosure:

Overall, the present disclosure provides with a protocol for producing multiple cell types of retina from induced pluripotent stem cell. The protocol described herein is a unified protocol that enables differentiation of iPSCs to retinal cells-photoreceptors, retinal pigmented epithelial cells and 3D retinal organoids. The single source of iPSC is grown under optimal condition of media with inhibitors and inducers relevant for differentiation of different cell lineage pertaining to the outer retina. Further, with the current protocol pigmentation of RPEs is observed by 30-50 days, and the same is consistent and sustained until 120 days and more. The protocol also does not require expensive and tedious use of transwell plates. The protocol provides with retinal cell derivatives that have better functional efficacy as well as consistent expression of the key markers earlier in the course of differentiation.

We claim:

1. A method for producing photoreceptor cells, retinal pigmented epithelial cells (RPEs) and retinal organoids from human pluripotent stem cells, the method comprising:
   A) culturing human pluripotent stem cells in a first media comprising pluripotent stem cell media and Y27632 such that non-adherent embryoid bodies (EBs) are obtained;
   B) maintaining the non-adherent EBs obtained in step A) in a second medium for 3-5 days, the second medium comprising DMEF/F12, knock out serum replacement (KOSR), sodium pyruvate, sodium bicarbonate, HEPES buffer, non-essential amino acids, insulin growth factor 1 (IGF1), N1 media supplements, activin A, nicotinamide, 4-(1,3,3a,4,7,7a-Hexahydro-1,3-dioxo-4,7-methano-2H-isoindol-2-yl)-N-8-quinolinyl-Benzamide, 4-[4-(1,3-benzodioxol-5-yl)-5-pyridin-2-yl-1H-imidazol-2-yl]benzamide, and 4-(6-(4-(piperazin-1-yl)phenyl)pyrazolo[1,5-a]pyrimidin-3-yl) quinoline;

C) culturing the non-adherent EBs obtained in step B) in the second medium on plates coated with an extracellular matrix for 4-8 days such that adherent EBs are obtained;

D) culturing the adherent EBs obtained in step C) in a third medium for 5-20 days such that neural rosettes and cells other than neural rosettes are obtained, wherein the third medium comprises: DMEM/F12, KOSR, sodium pyruvate, sodium bicarbonate, HEPES buffer, non-essential amino acids, and N1 media supplement;

E) selecting and culturing the neural rosettes obtained in step D) in the presence of the third medium, Y27632, DAPT, and SUS5402 on plates coated with extracellular matrix such that photoreceptor progenitors are obtained;

F) culturing the photoreceptor progenitors obtained in step E) in the third medium for 8-12 weeks such that photoreceptor cells are obtained;

G) culturing the cells other than neural rosettes obtained in step D) in the third medium for 5-7 days such that RPE progenitors are obtained;

H) culturing the RPE progenitors obtained in step G) in a fourth medium such that RPEs are obtained, wherein the fourth medium comprises MEMα modified, KOSR, glutamax, taurine, hydrocortisone, triido-thyronine, and N1 media supplement;

I) maintaining the non-adherent EBs obtained in step B) in the second medium for 8-10 days;

J) culturing the non-adherent EBs obtained in step I) in the third medium for 8-12 weeks such that retinal organoids are obtained.

2. The method according to claim 1, wherein step A) is performed by:
i) culturing human pluripotent cells in a first media comprising pluripotent stem cell media on an extracellular matrix until confluence;
ii) detaching the cells obtained in step A) i); and
iii) culturing the cells obtained in step A) ii) in the first medium on a non-adherent culture plate and Y27632 such that non-adherent EBs are obtained.

3. The method according to claim 2, wherein the non-adherent EBs obtained in step A) iii) are maintained in the first medium and Y27632 for 24-48 hours.

4. The method according to claim 2, wherein the extracellular matrix of step A) i) is vitronectin.

5. The method according to claim 1, wherein the extracellular matrix of step C) and step E) is vitronectin.

* * * * *